United States Patent
Busiashvili

(10) Patent No.: US 11,471,657 B1
(45) Date of Patent: Oct. 18, 2022

(54) DEVICE AND METHOD FOR MONITORING AND TREATING ADVANCED BRADYCARDIA

(71) Applicant: Stat Capsule Inc., Glendale, CA (US)

(72) Inventor: Yuri Busiashvili, Pacific Palisades, CA (US)

(73) Assignee: Stat Capsule Inc., Glendale, CA (US)

( * ) Notice: Subject to any disclaimer, the term of this patent is extended or adjusted under 35 U.S.C. 154(b) by 0 days.

(21) Appl. No.: 17/655,900

(22) Filed: Mar. 22, 2022

(51) Int. Cl.
*A61M 31/00* (2006.01)
*A61B 5/024* (2006.01)
*A61K 31/46* (2006.01)
*A61M 35/00* (2006.01)

(52) U.S. Cl.
CPC ......... *A61M 31/00* (2013.01); *A61B 5/02427* (2013.01); *A61B 5/02438* (2013.01); *A61K 31/46* (2013.01); *A61M 35/10* (2019.05); *A61B 2560/0487* (2013.01); *A61M 2205/186* (2013.01); *A61M 2205/3306* (2013.01)

(58) Field of Classification Search
CPC .................. A61M 31/00; A61M 35/10; A61M 2205/3306; A61M 2205/186; A61F 9/0026; A61F 9/0008; A61B 5/02427; A61B 5/02438
See application file for complete search history.

(56) References Cited

U.S. PATENT DOCUMENTS

| | | |
|---|---|---|
| 3,446,209 A | 5/1969 | Macha |
| 3,976,072 A | 8/1976 | Walker |
| 4,146,029 A * | 3/1979 | Ellinwood, Jr. ... A61N 1/37211 607/9 |
| 4,573,982 A | 3/1986 | Forbes et al. |
| 5,627,611 A | 5/1997 | Scheiner |
| 7,784,936 B2 | 8/2010 | Stinson |
| 8,770,743 B2 | 7/2014 | Tsubota et al. |
| 10,201,468 B2 | 2/2019 | Ahn |
| 10,624,781 B2 | 4/2020 | Ivri |
| 2004/0092548 A1 * | 5/2004 | Embleton ............. A61F 9/0008 514/310 |
| 2004/0207803 A1 | 10/2004 | Paukovits |
| 2009/0182291 A1 | 7/2009 | Eilat |

(Continued)

FOREIGN PATENT DOCUMENTS

| | | |
|---|---|---|
| CN | 203619766 U | 6/2014 |
| CN | 210277470 U | 4/2020 |

(Continued)

OTHER PUBLICATIONS

Panneton, W. Michael. "Controlled bradycardia induced by nasal stimulation in the muskrat, Ondatra zibethicus." Journal of the autonomic nervous system 30.3 (1990): 253-263. (Year: 1990).*

*Primary Examiner* — Nilay J Shah
(74) *Attorney, Agent, or Firm* — Ralph D. Chabot

(57) ABSTRACT

A device and method for monitoring the heart rate of a patient for a bradyarrhythmia event and thereafter administering medications is disclosed. The method comprises the steps of monitoring heart rate via at least one sensor secured to the neck or head of a patient; and if a bradyarrhythmia event is determined; applying an anticholinergic medication to the conjunctiva of at least one eye and releasing ammonia vapor in close proximity to the nostrils of a patient.

5 Claims, 3 Drawing Sheets

(56) References Cited

U.S. PATENT DOCUMENTS

| | | | |
|---|---|---|---|
| 2009/0247967 A1* | 10/2009 | Delli Paoli, Jr. | A61M 11/044 |
| | | | 604/521 |
| 2012/0179122 A1 | 7/2012 | Eilat et al. | |
| 2012/0253159 A1* | 10/2012 | Medina | A61B 5/14552 |
| | | | 600/340 |
| 2015/0018781 A1 | 1/2015 | Rinderknect et al. | |
| 2015/0148774 A1* | 5/2015 | Yao | A61M 5/1723 |
| | | | 604/504 |
| 2015/0370320 A1* | 12/2015 | Connor | A61B 5/1121 |
| | | | 345/173 |
| 2016/0296168 A1* | 10/2016 | Abreu | A61B 5/01 |
| 2016/0354240 A1 | 12/2016 | Chauhan et al. | |
| 2017/0071550 A1* | 3/2017 | Newberry | A61B 5/1495 |
| 2017/0156927 A1 | 6/2017 | Richter et al. | |
| 2020/0229973 A1 | 7/2020 | Tsubota | |
| 2020/0391029 A1 | 12/2020 | Mullins et al. | |

FOREIGN PATENT DOCUMENTS

| | | |
|---|---|---|
| KR | 20170123736 A | 11/2017 |
| RU | 2412676 C1 | 2/2011 |

\* cited by examiner

DEVICE AND METHOD FOR MONITORING AND TREATING ADVANCED BRADYCARDIA

FIELD OF THE INVENTION

The present invention relates to the field of heart treatment.

BACKGROUND

The human heart is "wired up" to allow the spark of an electric impulse to travel in the heart and cause electromechanical excitation. The impulse is generated in the natural pacemaker i.e. a group of nervous cells called sinus node, located in the right atrium. The impulse travels from the atria through the atrioventricular node (AVN) to ventricles to activate the sinus node causing mechanical contraction of the heart that results in blood circulation throughout the body. This mechanical contraction is interpreted as a pulse. Normally the pulse rate is above 50 beats per minute. For pathological conditions, the pulse rate may drop below 40 beats per minute.

Bradycardia less than 40 beats per minute and asystolic pauses longer than 3 seconds are treated successfully with a permanent pacemaker which, when surgically implanted, continuously monitors heart rhythm. When slow heart rhythm or asystole is detected, the pacemaker is activated and accelerates heart rhythm on demand. Millions of implanted permanent pacemakers prevent strokes, recurrent loss of consciousness, and cardiac arrest.

The reason is that indications for implantation of an electronic permanent pacemaker have to be documented; specifically, episodes of severe bradycardia or asystole. These spontaneous episodes may sometimes occur rarely and escape the monitoring devices, that are used to document presence of the dangerously slow heart rhythm.

There are external pacemakers/defibrillators available, but those are worn for life threatening tachyarrhythmias, to prevent cardiac arrest as opposed to bradycardic cardiac arrest.

There are two components of the autonomic nervous system that control the heart rate: A) cholinergic, largely represented by vagal nerve; it slows down the heart rate and atrioventricular conduction; and, B) adrenergic, that stimulates heart rate and improves atrioventricular conduction. Both systems are normally in balance. During the day, the adrenergic autonomous nervous system prevails during the time of activity; and, vagal nerves dominate the body physiology while the body is at rest, typically during the night.

With age or in certain pathological conditions, such as sick sinus syndrome or conduction abnormalities in the heart, severe bradycardia and episodes of prolonged asystolic pause may occasionally occur and go unnoticed or result in life threatening complications before any preventive measures can be applied.

For the last decade transfemoral aortic valve replacement (TAVR) has become very popular because of it's success with elderly patients having severe aortic stenosis. An aortic valve prosthesis is implanted via the femoral arterial approach and the patient is usually discharged from the hospital within 48 hours. The aortic valve ring is very close to the hearts electrical conduction system, in particular, the atrioventricular node, which is routinely traumatized by prosthetic valve carrying balloon during its inflation at the time of valve deployment. As a result, it's a common location for development of an advanced heart block after valve deployment. Roughly 10% of all patients undergoing TAVR require permanent pacemaker implantation to prevent episodes of complete heart block. However, with many other patients being discharged from the hospital within 48 hours, episodes of transient heart block may occur days or weeks later, during the 2-3 month healing process.

As a result of a TAVR procedure, the surrounding tissues are injured and the healing period can takes weeks for the inflammation and trauma resulting from the stent placement to subside, just as for other myocardial injuries. In some patients, TAVR will cause the formation of scar tissue which can alter the normal electronic impulse or atrio-ventricular conduction and lead to atrioventricular conduction delay, or high degree atrioventricular block. The extreme expression of heart block is complete heart block (CHB).

In CHB, an electric impulse is not conducted to the pumping chamber ventricles, and the heart ceases to contract, which is a condition called cardiac standstill. A cardiac standstill lasting longer than 15 seconds is considered cardiac arrest.

There is no wearable medical device that is able to continually monitor heart rate, detect life threatening bradycardia and/or asystole, alert the user of its onset and automatically immediately discharge non electronic therapy on demand.

Some wearable heart rate monitors use photoplethysmography (PPG) sensors to measure heart rate. PPG sensors are typically worn on the wristband for convenience, but can be applied to the skin of the earlobe as well for heart rate monitoring.

It is well known sinus bradycardia or sudden onset of atrioventricular block can be treated with either intravenous administration of Atropine—an anticholinergic, or an adrenaline like sympathomimetic substance. Since discharged patients do not have access to intravenous delivered medication, the fastest way to increase the endogenous adrenaline production is by inhaling ammonia vapor which works through the olfactory reflex within seconds after inhalation. The need exists to monitor patients having sick sinus syndrome, especially at night to detect and prevent life-threatening bradycardia.

Some percentage of the patients experience syncope, collapse or die with sudden development of a high degree atrioventricular block progressing to CHB. Atropine intramuscularly or intravenously is used in a hospital setting to improve atrioventricular conduction.

Atropine has also been used for dilation of a pupil during an eye exam. Some of the Atropine applied to the eye is absorbed to the general blood circulation.

A need exists for monitoring of discharged patients following a TAVR procedure for onset of CHB and should such a condition arise, provide medication to treat the condition.

SUMMARY OF THE INVENTION

Described herein is a device and method to monitor a patient for a bradyarrhythmia event and if required, deliver medications to the patient. More specifically, an anticholinergic medication such as Atropine administered to the conjunctiva; and release of an inhalant that causes the body to release Adrenaline via an olfactory unconditional reflex.

This invention is designed to treat episodes of asystolic arrest which can follow the transition of the rhythm from rapid atrial fibrillation to sinus bradycardia and/or suddenly developed high degree atrioventricular block, especially in the first few weeks following a TAVR procedure.

Specifically, TAVR related blockage can occur within seconds, causing the patient to pass out or progress to cardiac arrest. For patients that are susceptible to this condition, it is vital that life-saving medication be immediately available.

Therefore, the invention is directed to monitoring for a bradyarrhythmia event and should that event occur, an anticholinergic medication such as Atropine will be administered to the conjunctiva area of the eye and ammonia vapor will be released for inhalation to cause the body to release Adrenaline via an olfactory unconditional reflex. Administration of the anticholinergic medication should occur within ten seconds of the bradyarrhythmia event. Inhalation of an inhalant such as ammonia vapor in combination with the administration of an anticholinergic medication to the conjunctiva area of the eye, increases the chance for a patient to survive a bradyarrhythmia event event outside of a hospital setting.

As defined herein, the term bradyarrhythmia event means either: 1) heart rate below 40 beats per minute; or, b) no heart beat for at least 3 seconds.

In a preferred embodiment, a device is provided to monitor the heart rate and administer medication. This is accomplished by an eyeglass frame designed to automatically administer anticholinergic medication to the conjunctiva area of the eye as well as releasing ammonia vapor automatically or manually for inhalation. The vapor will cause the body to release Adrenaline via an olfactory unconditional reflex. Inhalation of the ammonia vapor in combination with the administration of an anticholinergic medication to the conjunctiva area of the eye, increases the chance of a patient surviving an asystolic event outside of a hospital setting; particularly when the patient is asleep.

The device comprises an eyeglass frame having as part of the frame, or connected thereto, at least one PPG sensor, a reservoir containing an anticholinergic medication and a means for delivery of the medication to the conjunctiva area of the eye. In one embodiment an ammonia inhalant capsule is attached to the eyeglass frame within a compartment designed to release the vapor from the capsule in response to the patient experiencing a bradyarrhythmia event. Optionally, the device can include vibration and/or audible alerts for the patient.

The PPG sensor is used to monitor for a bradyarrhythmia event and is attached to the neck or head of a patient. The sensor can be located on one of the temples of the frame or more preferably, is operably connected by either a wire or wirelessly connected to a module mounted to the frame which measures data from the sensor. Thus, the sensor can be attached to the body at various locations such as inside the ear canal, on the ear lobe, behind the ear on the skull, or on the neck.

Following the recognition of a bradyarrhythmia event from data received from the PPG sensor, Atropine is applied to the conjunctiva of preferably both eyes; either as eye drops or as a mist.

In another embodiment, to potentiate the antibradycardia effect of Atropine, an ammonia inhalant capsule is mounted to the eyeglass frame which can be manually crushed. By being attached to the eyeglass frame, the inhalant capsule is in sufficiently close proximity to the nostrils of the patient for the vapor released from the capsule to be inhaled. Inhalation will cause an olfactory unconditional reflex and endogenous Adrenaline release, which in turn almost immediately increases the heart rate and improves atrioventricular conduction preventing prolonged asystole.

Since the recommended time required for healing of the tissue around the aortic valve prosthesis can be as long as 10-11 weeks post TAVR procedure, the use of the device should be for the same period of time.

The device includes a medication reservoir that can be integrated with the eyeglass frame or can be operatively connected thereto.

Data from the PPG sensor is used to monitor for a bradyarrhythmia event and the anticholinergic medication is applied onto the conjunctiva of either eyeball. The medication, for example, could be a 0.1% Atropine solution released as a drip or mist and the reservoir would contain about 1 cc of 0.1% Atropine.

Atropine delivered onto the conjunctiva is almost immediately absorbed and will increase heart rate, and temporarily reverse profound bradycardia. The timely administration of medication can prevent progression of severe bradycardia to asystole or higher degree atrioventricular block from occurring.

DETAILED DESCRIPTION OF THE PREFERRED EMBODIMENT

The figures presented herein are for illustrative purposes and the illustrated parts are not necessarily shown in correct proportion or scale.

The device and methodology described herein is specifically directed to patients who have undergone a TAVR procedure and have been discharged from the hospital. For these patients, the risk of experiencing a bradyarrhythmia event event within weeks of hospital discharge is high.

The method for monitoring heart rate and dispensing a medication comprises the steps of:

monitoring heart rate via at least one sensor attached to the neck or head of a patient to detect the occurrence of a bradyarrhythmia event; and, upon detection of a bradyarrhythmia event, applying an anticholinergic medication to the conjunctiva of at least one eye of the patient and releasing ammonia vapor in close proximity to a patient's nostrils.

The release of ammonia vapor can be before, concurrently or subsequent to application of the anticholinergic medication.

Figure 1:
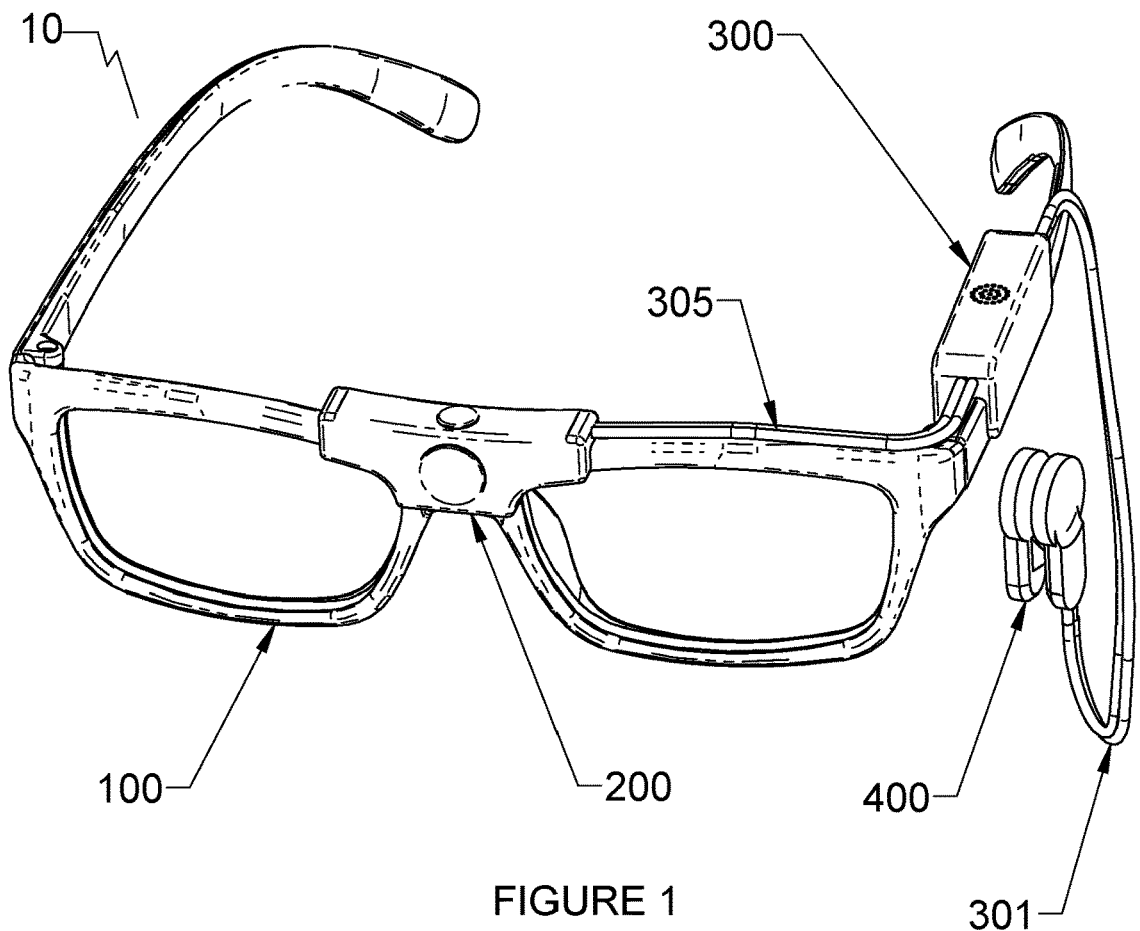
FIG. 1 is a perspective view of one embodiment of the device.

The methodology can be implemented by device 10 illustrated in FIG. 1. Device 10 comprises an eyeglass frame 100 having a sprayer 200 and a module 300.

Figure 3:
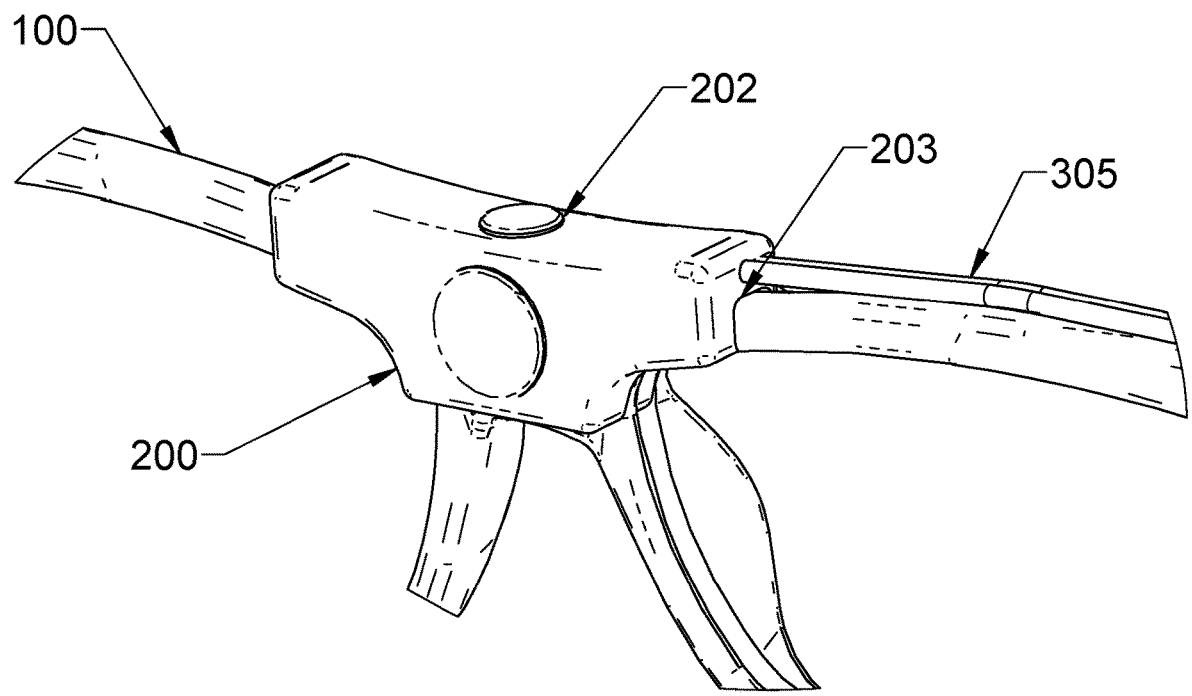
FIG. 3 is a close up view of the bridge portion of the device illustrated in FIG. 1.
Figure 4:
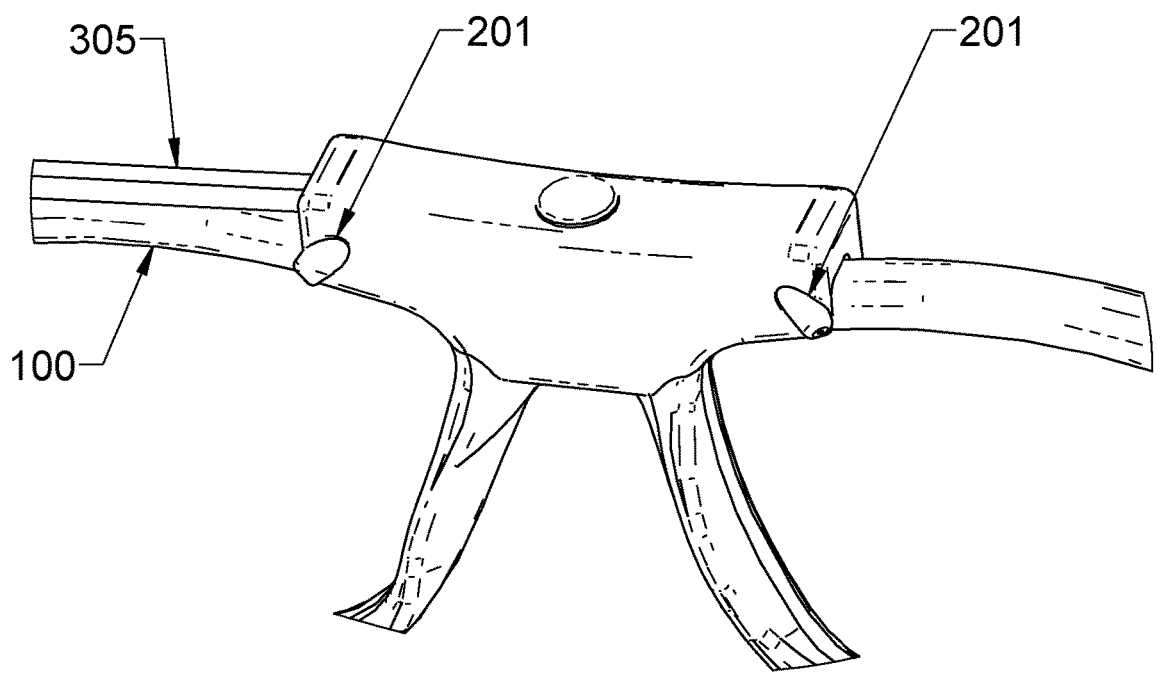
FIG. 4 is an alternate close up view of the bridge portion of the device illustrated in FIG. 1.

Sprayer 200 includes a reservoir (not shown) for storage of an anticholinergic medication such as Atropine. As best illustrated in FIG. 3, sprayer 200 includes a removable cap 202 for refilling the reservoir and a snap-on recess 203. Sprayer 200 can be designed to fit on the bridge of eyeglass frame 100 with recess 203 ensuring a secure attachment. Sprayer 200 includes a pair of nozzles 201 as best shown in FIG. 4. These nozzles discharge the medication from sprayer 200 to the conjunctiva of the patient.

Figure 2:
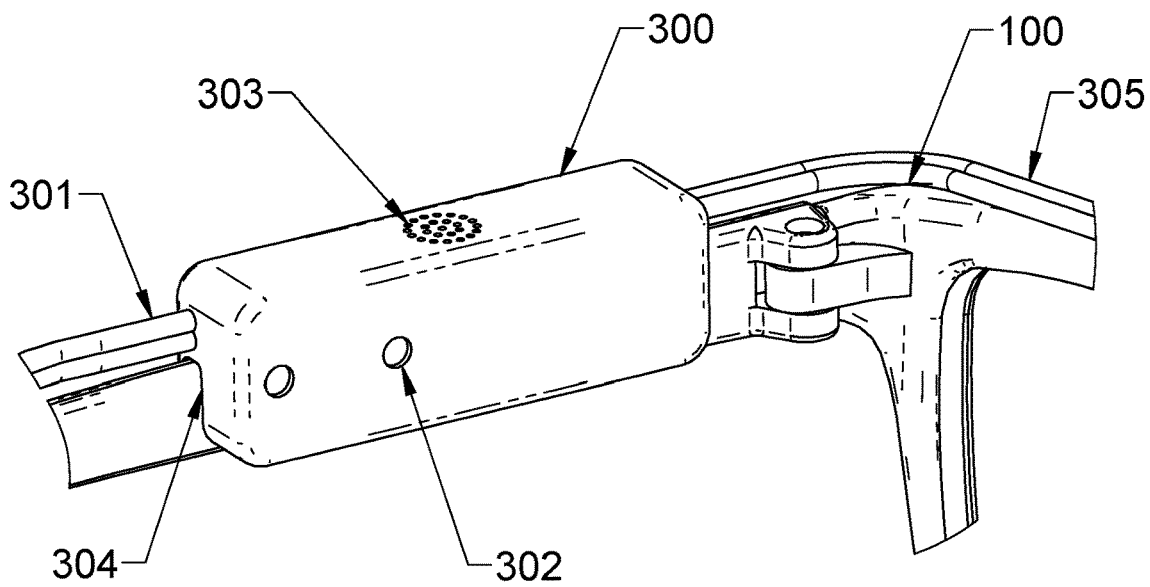
FIG. 2 is a close up view of the module of the device illustrated in FIG. 1.

Module 300 is best illustrated in FIG. 2 and comprises a wire 301 for operative connection to a PPG sensor 400 as will be discussed later. Wire 305 operably connects module 300 to sprayer 200. Module 300 further comprises a charging terminal 302 for charging an internal battery (not shown), an audio speaker 303 and a vibration unit (not shown), and a snap-on recess 304 to securely attach Module 300 to eyeglass frame 100.

Figure 5:
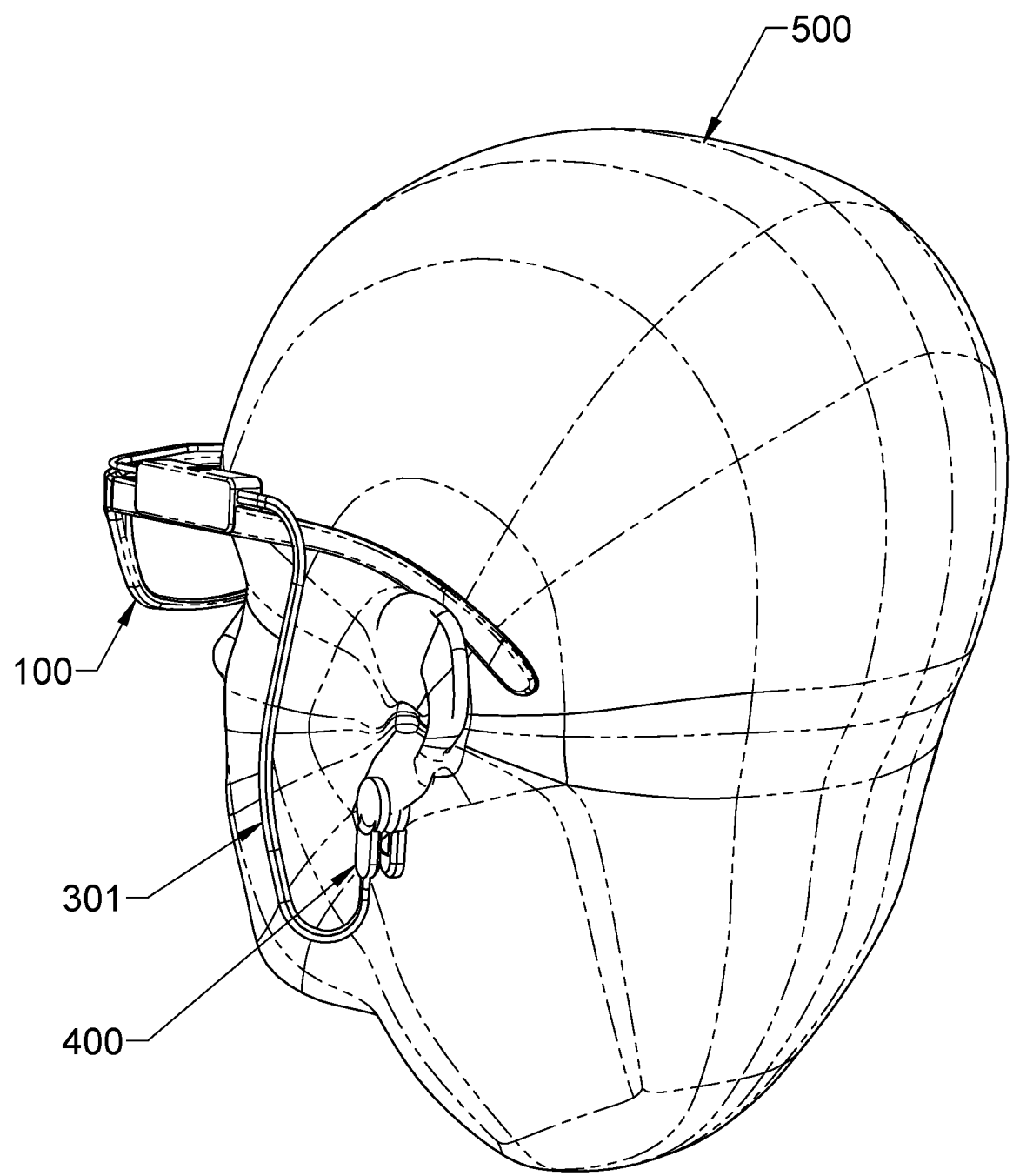
FIG. 5 is a prospective view of the device on a user.

In order for device 10 to be worn while the patient sleeps, a band (not shown) connected on either end to respective temples of frame 100 is used to maintain the positioning of device 10 to the patient's head. Wire 301 connects module 300 to PRG sensor 400 which in turn is attached to a patient's earlobe shown as part of human head 500 in FIG. 5.

In practice, a patient wearing device 10 will have his heart rate monitored by PPG sensor 400. If the monitored heart rate falls below 40 beats per minute or if there is no heart beat for at least 3 seconds, a bradyarrhythmia event will have occurred and an anticholinergic medication will be dispensed through nozzles 201 for administration to the conjunctiva of the patient's eyes within 10 seconds as well as the release of ammonia vapor from ports 303 of module 300 which is in close proximity to the nostrils of the patient. Module 300 is also equipped with a speaker and vibration device (not shown) for alerting the patient, particularly if asleep.

I claim:

1. A method for monitoring a patient's heart rate using at least one sensor attached to the neck or head of the patient and dispensing a medication onto the conjunctiva of at least one eye automatically in response to a bradyarrhythmia event comprising the steps of:
   monitoring heart rate via the at least one sensor attached to the neck or head of the patient to determine a bradyarrhythmia event; and,
   if a bradyarrhythmia event has occurred, automatically dispensing an anticholinergic medication to the patient and automatically releasing ammonia vapor.

2. A device for monitoring a patient's heart rate and dispensing a medication onto the conjunctiva of at least one eye comprising:
   an eyeglass frame having a bridge;
   a photoplethysmography sensor;
   a module connected to the eyeglass frame comprising: an input for operable connection to the photoplethysmography sensor; an ammonia inhalant; and, an alert mechanism selected from the group consisting of audible, vibration or both; and,
   a spray mechanism attached upon the bridge of the frame having a reservoir for containing a predetermined amount of anticholinergic medication; the spray mechanism having at least one nozzle for discharging the liquid medication.

3. The device of claim 2 wherein the anticholinergic medication is Atropine.

4. The device of claim 2 further comprising a wire for operable connection of the photoplethysmography sensor to the module.

5. A method for monitoring a patient's heart rate using at least one sensor attached to the neck or head of the patient and dispensing a medication onto the conjunctiva of at least one eye automatically in response to a bradyarrhythmia event comprising the steps of:
   monitoring heart rate via the at least one sensor attached to the neck or head of the patient to determine a bradyarrhythmia event; and,
   upon detection of a bradyarrhythmia event, thereafter applying an anticholinergic medication to the conjunctiva of at least one eye of the patient and releasing ammonia vapor.

\* \* \* \* \*